(12) United States Patent
Haraikawa et al.

(10) Patent No.: US 10,791,949 B2
(45) Date of Patent: Oct. 6, 2020

(54) COMPUTATION APPARATUS, CARDIAC ARRHYTHMIA ASSESSMENT METHOD THEREOF AND NON-TRANSITORY COMPUTER-READABLE RECORDING MEDIUM

(71) Applicant: Kinpo Electronics, Inc., New Taipei (TW)

(72) Inventors: Koichi Haraikawa, New Taipei (TW);
Jen-Chien Chien, New Taipei (TW);
Chia-Chun Kuo, New Taipei (TW);
Chien-Hung Lin, New Taipei (TW);
Yi-Ta Hsieh, New Taipei (TW);
Tsui-Shan Hung, New Taipei (TW);
Yin-Tsong Lin, New Taipei (TW)

(73) Assignee: Kinpo Electronics, Inc., New Taipei (TW)

( * ) Notice: Subject to any disclaimer, the term of this patent is extended or adjusted under 35 U.S.C. 154(b) by 314 days.

(21) Appl. No.: 15/942,411

(22) Filed: Mar. 30, 2018

(65) Prior Publication Data
US 2019/0209036 A1 Jul. 11, 2019

(30) Foreign Application Priority Data
Jan. 10, 2018 (TW) .............................. 107100909 A

(51) Int. Cl.
*A61B 5/0402* (2006.01)
*A61B 5/0468* (2006.01)
*A61B 5/046* (2006.01)
*A61B 5/0472* (2006.01)

(52) U.S. Cl.
CPC .......... *A61B 5/04028* (2013.01); *A61B 5/046* (2013.01); *A61B 5/0468* (2013.01); *A61B 5/0472* (2013.01)

(58) Field of Classification Search
CPC ............................ A61B 5/04028; A61B 5/046
(Continued)

(56) References Cited

U.S. PATENT DOCUMENTS 6,480,734 B1 11/2002 Zhang et al.
6,490,478 B1 12/2002 Zhang et al.
(Continued)

FOREIGN PATENT DOCUMENTS

CN  102971045  3/2013
CN  105163803  12/2015
(Continued)

OTHER PUBLICATIONS

"Office Action of Japan Counterpart Application," dated Apr. 16, 2019, p. 1-p. 4.
(Continued)

*Primary Examiner* — Nadia A Mahmood
(74) *Attorney, Agent, or Firm* — JCIPRNET

(57) ABSTRACT

A computation apparatus, a cardiac arrhythmia assessment method thereof and a non-transitory computer-readable recording medium are provided. In the method, electrocardiography (ECG) signal is obtained. Whether the ECG signal is conformed to a first abnormal rhythm symptom is determined. Then, whether the ECG signal is conformed to a second abnormal rhythm symptom different from the first abnormal rhythm symptom is determined based on the determined result of the first abnormal rhythm symptom. Accordingly, multiple abnormal rhythm assessments are integrated, the subsequent assessment is speeded-up and optimized according to the determined result of a previous assessment, so as to enable to implement on a handheld apparatus.

15 Claims, 3 Drawing Sheets

(58) Field of Classification Search
USPC .......................................................... 606/515
See application file for complete search history.

(56) References Cited

U.S. PATENT DOCUMENTS

| | | | |
|---|---|---|---|
| 7,715,916 | B2 | 5/2010 | Haefner |
| 9,161,705 | B2 | 10/2015 | Tamil et al. |
| 9,420,956 | B2 | 8/2016 | Gopalakrishnan et al. |
| 2007/0293896 | A1* | 12/2007 | Haefner ......... A61B 17/320068 607/6 |

FOREIGN PATENT DOCUMENTS

| | | |
|---|---|---|
| JP | 2005511166 | 4/2005 |
| JP | 2008507339 | 3/2008 |
| JP | 2008517712 | 5/2008 |
| JP | 2016140689 | 8/2016 |
| TW | 200824650 | 6/2008 |
| TW | 201617025 | 5/2016 |

OTHER PUBLICATIONS

Dingfei Ge et al.,"Cardiac arrhythmia c;assification using autoregressive modeling," BioMedical Engineering Online, BioMed central, Nov. 13, 2002, pp. 1-13.

"Office Action of Taiwan Counterpart Application", dated Jan. 4, 2019, p. 1-p. 5.

Hamilton, "Open Source ECG Analysis Software Documentation," EP Limited, 2002 pp. 1-33.

Zhou et al., "A real-time atrial fibrillation detection algorithm based on the instantaneous state of heart rate," PLOS One, Sep. 2015, pp. 1-16.

Lin et al., "A modular integrating algorithm for multiple arrhythmia detection," In Proceedings of the IEEE International Conference on Communication Problem-Solving (ICCP), Sep. 2016, pp. 1-2.

Lo et al., "A new method to estimate the amplitude spectrum analysis of ventricular fibrillation during cardiopulmonary resuscitation," Resuscitation, Nov. 2013, pp. 1505-1511.

Alonso-Atienza et al., "Feature selection using support vector machines and bootstrap methods for ventricular fibrillation detection," Expert Systems with Applications, Feb. 2012, pp. 1956-1967.

Anas et al., "Exploiting correlation of ECG with certain EMD functions for discrimination of ventricular fibrillation," Computers in Biology and Medicine, Feb. 2011, pp. 110-114.

Clayton et al., "Estimation of the ECG signal spectrum during ventricular fibrillation using thefast Fourier transform and maximum entropy methods," In Proceedings of the IEEE Computers in Cardiology, Sep. 1993, pp. 867-870.

Afonso et al, "Detecting ventricular fibrillation," IEEE Engineering in Medicine and Biology Magazine, Mar. 1995, pp. 152-159.

Sadrawi et al., "Arrhythmia Evaluation in Wearable ECG Devices," Sensors, Oct. 25, 2017, pp. 1-14.

* cited by examiner

COMPUTATION APPARATUS, CARDIAC ARRHYTHMIA ASSESSMENT METHOD THEREOF AND NON-TRANSITORY COMPUTER-READABLE RECORDING MEDIUM

CROSS-REFERENCE TO RELATED APPLICATION

This application claims the priority benefit of Taiwan application serial no. 107100909, filed on Jan. 10, 2018. The entirety of the above-mentioned patent application is hereby incorporated by reference herein and made a part of this specification.

BACKGROUND OF THE INVENTION

Field of the Invention

The invention relates to a physiological state assessment, and particularly relates to a computation apparatus and cardiac arrhythmia assessment method thereof.

Description of Related Art

An electrocardiography (ECG) signal is an important basis for assessing abnormal heart rhythm. In a heartbeat cycle of a normal heart, a pacing impulse is generated in a sinoatrial node (SA node) and spread to the left and right atriums, collected in an atrioventricular node (AV node), and the impulse continues along bundles of His, left and right spreading down throughout the ventricle. Depolarization is immediately followed by repolarization, and rhythmic heartbeats are produced by the self-repeating sequence of depolarization, impulse-contraction, and repolarization. Under abnormal circumstances, atrial and atrioventricular node and ventricular ectopic beat seize control of the pacing through the AV node, and result in ectopic beats.

Since a part of the assessment of abnormal rhythm symptoms require a large amount of data computation, most hardware requirements used for cardiac arrhythmia assessments are higher, and it is difficult to provide portable and real-time detection. Even though some algorithm can be realized on smartphones or other handheld apparatuses, it is also limited to the assessment of a single symptom. Furthermore, prior art is often based on independent judgements of various types of abnormal rhythm symptoms, and fails to consider the misjudgment that could be easily caused by the influence between each other, thus, is less accurate. Accordingly, it can be known that existing techniques for assessing cardiac arrhythmia still need to be improved.

SUMMARY OF THE INVENTION

In view of this, the invention provides a computation apparatus, a cardiac arrhythmia assessment method thereof and a non-transitory computer-readable recording medium, integrating multiple symptoms of cardiac arrhythmia assessments, further providing effects of high accuracy under light computation.

The cardiac arrhythmia assessment method of the invention includes the following steps: obtaining an ECG signal, determining whether the ECG signal is conformed to a first abnormal rhythm symptom, and determining whether the ECG signal is conformed to a second abnormal rhythm symptom based on the determined result of the first abnormal rhythm symptom, and the second abnormal rhythm symptom is different from the first abnormal rhythm symptom.

In an exemplary embodiment of the invention, the foregoing determining whether the ECG signal is conformed to a second abnormal rhythm symptom based on the determined result of the first abnormal rhythm symptom, includes the following steps: if the determined result of the first abnormal rhythm symptom is conformed, the feature of the ECG signal is modified and used for determining the second abnormal rhythm symptom.

In an exemplary embodiment of the invention, the foregoing first abnormal rhythm symptom is a ventricular premature contraction (VPC), and modifying the feature of the ECG signal includes the following steps: correcting an R-wave position in the ECG signal used for determining the second abnormal rhythm symptom, and accordingly adjust an R-R interval.

In an exemplary embodiment of the invention, the foregoing determining whether the ECG signal is conformed to a second abnormal rhythm symptom based on the determined result of the first abnormal rhythm symptom, includes the following step: if the determined results of the first abnormal rhythm symptom and the second abnormal rhythm symptom are both abnormal heart rhythm, it is determined that only one of the first heartbeat abnormality symptom and the second heartbeat abnormality symptom is conformed, and correcting the determined result of the other is not conformed.

In an exemplary embodiment of the invention, the foregoing first abnormal rhythm symptom is an atrial fibrillation (AF), and the second abnormal rhythm symptom is an atrial premature contraction (APC), and determining that only one of the first abnormal rhythm symptom and the second abnormal rhythm symptom is conformed, and correcting the determined result of the other is not conformed, includes the following step: determining only conforming to the AF and not conforming to the APC.

In an exemplary embodiment of the invention, the foregoing first abnormal rhythm symptom is a VPC, and the second abnormal rhythm symptom is an APC, and determining that only one of the first abnormal rhythm symptom and the second abnormal rhythm symptom is conformed, and correcting the determined result of the other is not conformed, includes the following step: determining only conforming to the VPC and not conforming to the APC.

In an exemplary embodiment of the invention, the foregoing first abnormal rhythm symptom is an AF, and the second abnormal rhythm symptom is a ventricular fibrillation (VF), and determining that only one of the first abnormal rhythm symptom and the second abnormal rhythm symptom is conformed, and correcting the determined result of the other is not conformed, includes the following step: determining only conforming to the VF and not conforming to the AF.

In an exemplary embodiment of the invention, the foregoing after determining whether the ECG signal is conformed to the second abnormal rhythm symptom based on the determined result of the first abnormal rhythm symptom, further includes the following steps: determining the ECG signal is conformed to a third abnormal rhythm symptom based on the determined result of at least one of the first abnormal rhythm symptom and the second abnormal rhythm symptom, and the third abnormal rhythm symptom is different from the second abnormal rhythm symptom.

A computation apparatus of the invention includes a transmission interface and a processor. The transmission interface obtains an ECG signal. The processor coupled to the transmission interface determines whether the ECG signal is conformed to the first abnormal rhythm symptom, and determines whether the ECG signal is conformed to the second abnormal rhythm symptom based on the determined result of the first abnormal rhythm symptom, and the first abnormal rhythm symptom is different from the second abnormal rhythm symptom.

In an exemplary embodiment of the invention, if the determined result of the first abnormal rhythm symptom is conformed, the processor modifies the feature of the ECG signal, and is used to determine the second abnormal rhythm symptom.

In an exemplary embodiment of the invention, the foregoing first abnormal rhythm symptom is a VPC, and the processor corrects the R-wave position in the ECG signal used for determining the second abnormal rhythm symptom, and accordingly adjusts the R-R interval.

In an exemplary embodiment of the invention, if the determined results of the first abnormal rhythm symptom and the second abnormal rhythm symptom are both abnormal heart rhythm, the processor determines that only one of the first abnormal rhythm symptom and the second abnormal rhythm symptom is conformed, and the correcting the determined result of the other is not conformed.

In an exemplary embodiment of the invention, the foregoing first abnormal rhythm symptom is an AF, and the second abnormal rhythm symptom is an APC, and the processor determines that only the AF is conformed and the APC is not conformed.

In an exemplary embodiment of the invention, the foregoing first abnormal rhythm symptom is a VPC, and the second abnormal rhythm symptom is an APC, and the processor determines that only the VPC is conformed and the APC is not conformed.

In an exemplary embodiment of the invention, the foregoing first abnormal rhythm symptom is an AF, and the second abnormal rhythm symptom is a VF, and the processor determines that only the VF is conformed and the AF is not conformed.

In an exemplary embodiment of the invention, the foregoing processor determines whether the ECG signal is conformed to the third abnormal rhythm symptom based on the determined result of at least one of the first abnormal rhythm symptom and the second abnormal rhythm symptom, and the third abnormal rhythm symptom is different from the second abnormal rhythm symptom.

The non-transitory computer-readable recording medium of the invention records a program code which is loaded by a processor of the computation apparatus to perform the following steps: obtaining an ECG signal, determining whether the ECG signal is conformed to a first abnormal rhythm symptom, determining whether the ECG signal is conformed to a second abnormal rhythm symptom based on the determined result of the first abnormal rhythm symptom, and the second abnormal rhythm symptom is different from the first abnormal rhythm symptom.

Based on the foregoing, in order to effectively improve the accuracy of judgement, an exemplary embodiment of the invention corrects the assessment of another abnormal rhythm symptom based on the determined result of a certain abnormal rhythm symptom, so that it is not necessary to use an overly complicated algorithm to assess a single abnormal rhythm symptom, thereby obtaining the analysis result instantly and quickly, which can be applied onto a handheld apparatus. Furthermore, the subject of assessment may be increased or decreased according to needs, highly expanding the flexibility of adjustment.

To make the foregoing features and advantages of the invention more comprehensible, embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DETAILED DESCRIPTION OF DISCLOSED EMBODIMENTS

Figure 1:
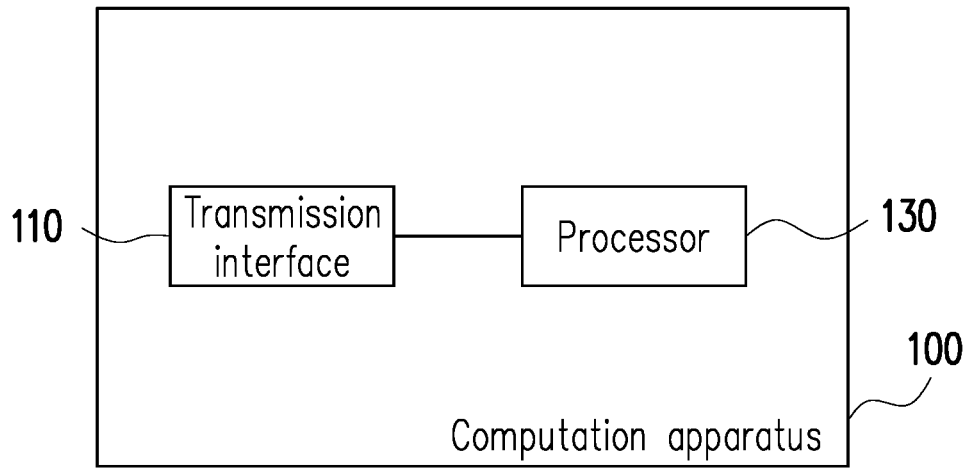
FIG. 1 is a component block diagram of a computation apparatus according to an exemplary embodiment of the invention.

FIG. 1 is a component block diagram of a computation apparatus 100 according to an exemplary embodiment of the invention. Referring to FIG. 1, the computation apparatus 100 may be a smart phone, a tablet computer, a computer host, a server or other equipment (the preferred embodiment is an aspect of a lightweight handheld apparatus such as a smart phone or a tablet computer), and at least includes but is not limited to a transmission interface 110 and a processor 130.

The transmission interface 110 may be Wi-Fi, Bluetooth, various types of parallel or serial bus interfaces, and used to obtain ECG signals based on supported transmission technology.

The processor 130 is connected to the transmission interface 110, and may be a central processing unit (CPU), or other programmable microprocessor of general purpose or special purpose, a digital signal processor (DSP), a programmable controller, an application specific integrated circuit (ASIC), or other similar components or a combination of the above components. In an exemplary embodiment of the invention, the processor 130 is used to execute all operations of the computation apparatus 100, and may process the ECG signals.

Figure 2:
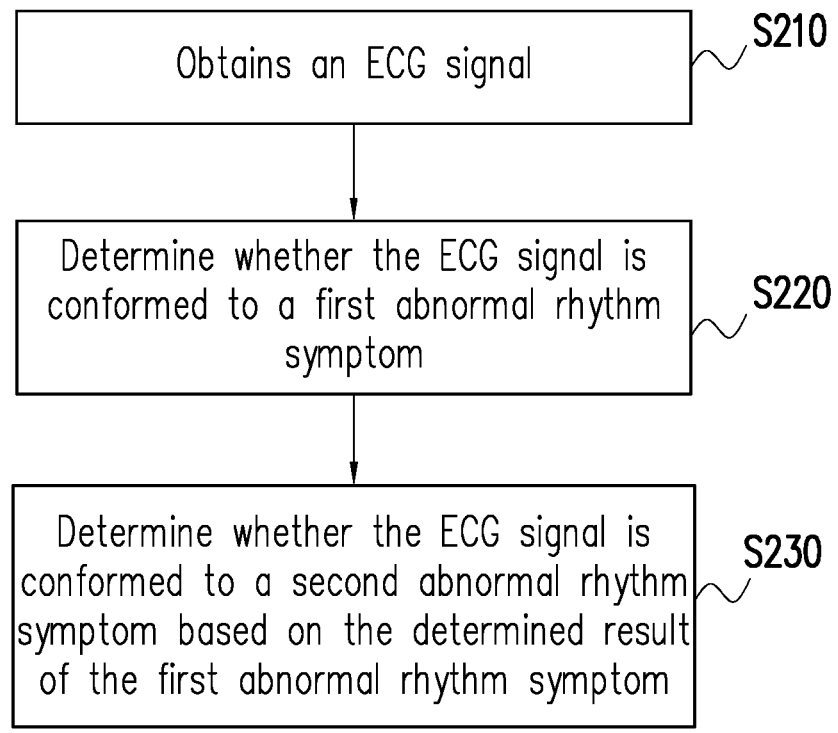
FIG. 2 is a flow chart of a cardiac arrhythmia assessment method according to an exemplary embodiment of the invention.

In order to facilitate understanding of the operational flow of the invention, several exemplary embodiments will be described in detail below. FIG. 2 is a flow chart of a cardiac arrhythmia assessment method according to an exemplary embodiment of the invention. Referring to FIG. 2, hereinafter, various components and modules of the computation apparatus 100 will be used to describe the method according to an exemplary embodiment of the invention. The various processes of the method may be adjusted according to circumstances of the embodiments, and are not limited thereto.

Through the transmission interface 110, the processor 130 obtains the ECG signal (step S210) via an external wearable device (set with an ECG sensor), or a storage (for example, a flash memory, a multimedia card and other storage media) of the computation apparatus 100, or even a built-in ECG sensor. In other words, the transmission interface 110, the computation apparatus 100 may obtain the ECG signal via an internal or an external ECG sensor, and an exemplary embodiment of the invention does not limit the source of the ECG signal. In order to achieve the function of instant detection, the processor 130 may periodically (for example, every 5 and 10 minutes, and every 10 and 15 seconds and so on) or at any time request or directly receive the ECG signal of the ECG sensor.

Next, the processor 130 determines whether the ECG signal is conformed to a first abnormal rhythm symptom (step S220). Specifically, the first abnormal rhythm symptom may be a VPC, an AF, an APC, a VF, a paroxysmal supraventricular tachycardia (PSVT), or an atrial flutter and other types of abnormal rhythm symptoms. Based on different abnormal rhythm symptoms, the processor 130 will use different heart rhythm assessment algorithm to determine whether the corresponding abnormal rhythm symptoms are conformed. For example, the VPC uses the analysis method proposed by Hamilton, P. S. Open Source ECG Analysis Software Documentation; EP Limited: Somerville, Mass., USA, 2002 (Document 1) can be used in the VPC assessment; and Zhou, X.; Ding, H.; Wu, W.; Zhang, Y. A real-time atrial fibrillation detection algorithm based on the instantaneous state of heart rate. PLoS ONE 2015, 10, e0136544 (Document 2) can be used in the AF assessment, and so on.

It is worth noting that, in an exemplary embodiment of the invention, the processor 130 will determine whether the ECG signal is conformed to a second abnormal rhythm symptom (step S230) based on the determined result of the first abnormal rhythm symptom, and the second abnormal rhythm symptom (reference may be made to the description aspect of the first abnormal rhythm symptom) is different from the first abnormal rhythm symptom. Specifically, since the ECG signal conformed to part of the abnormal rhythm symptoms may affect the assessment of other abnormal rhythm symptoms (there may be a situation of misjudgment), therefore, if the determined result of the first abnormal rhythm symptom in step S220 is conformed, the processor 130 may modify the feature of the ECG signal. For example, correcting an R-wave position, adjusting an R-R interval, averaging the R-R interval and other features, and using the modified ECG signal as an input parameter of assessment of the second abnormal rhythm symptom. On the other hand, the ECG signal conformed to part of the abnormal rhythm symptoms may be similar to some features in the ECG signal of other abnormal rhythm symptoms, to cause a situation of misjudgment from happening. Therefore, if the determined results of the first abnormal rhythm symptom and the second abnormal rhythm symptom are both abnormal heart rhythm, the processor 130 will determine that only one of the first abnormal rhythm symptom and the second abnormal rhythm symptom is conformed based on an existing test result of a database, and correcting the determined result of the other is not conformed. For example, the determined result of the first abnormal rhythm symptom is conformed to the AF, and the determined result of the second abnormal rhythm symptom is conformed to the APC, and the processor determines that only the AF is conformed and the APC is not conformed.

Furthermore, in order to integrate more types of multiple abnormal rhythm assessments, the processor 130 may further determine whether the ECG signal is conformed to a third abnormal rhythm symptom (reference may be made to the description aspect of the first abnormal rhythm symptom) based on the determined result of the first abnormal rhythm symptom and/or the second abnormal rhythm symptom, and the third abnormal rhythm symptom is different from the second abnormal rhythm symptom. By analogy, the computation apparatus 100 may also integrate a fourth, a fifth or even more types of abnormal rhythm assessments, and correct subsequent determined results based on the determined result obtained, increasing the determination speed by a serial operation mode, and improving the accuracy by an information feedback mode. It should be noted that, in an exemplary embodiment of the invention, the sequence and number of each abnormal rhythm assessments may be changed according to actual needs, and the computation apparatus 100 can further provide options for users to choose from.

Figure 3:
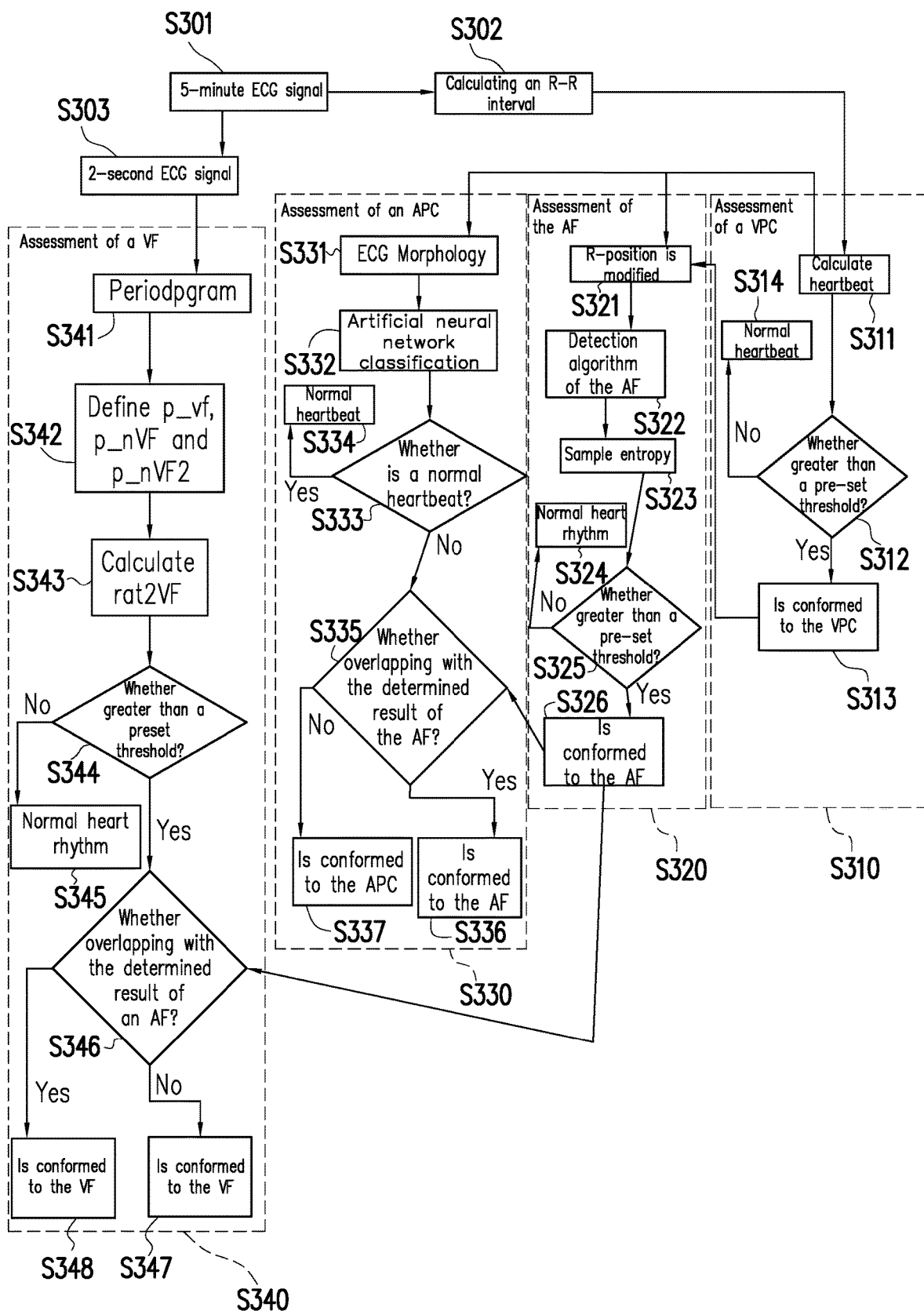
FIG. 3 is a flow chart of four types of symptoms assessment methods according to an exemplary embodiment of the invention.
Figure 4A:
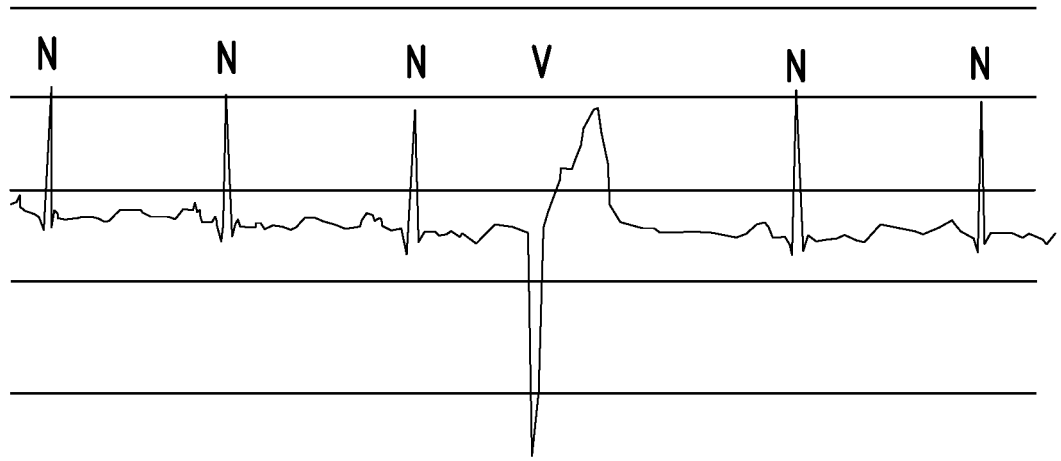
FIG. 4A and FIG. 4B are an example describing an ECG signal before and after correction.

For the convenience of the reader to understand the spirit of the invention, another exemplary embodiment is provided below to describe a flow chart illustrating four types of symptoms assessment methods. Referring to FIG. 3, the processor 130 receives a user-selected operation or pre-set four types of abnormal rhythm assessments, which are respectively, the VPC, the AF, the APC, and the VF. The computation apparatus 100 first obtains an ECG signal (step S301) of sufficient length of time (for example, 5 minutes) from an external wearable detection device via a Bluetooth low energy (BLE) technology to calculate an R-R interval (step S302). For example, FIG. 4A is an example of the ECG signal. The processor 130 detects the R-wave from the original ECG signal, the R-wave position is marked as N in the drawing, and the distance between two adjacent R-waves is the R-R interval.

Regarding the assessment of the VPC (step S310), an exemplary embodiment of the invention uses a heartbeat detection method as proposed by the foregoing Document 1, whereby the processor 130 calculates the heartbeat (step S311) according to the R-R interval, and determines whether the heartbeat width of a QRST waveform is greater than a pre-set threshold (for example, 100 ms) (step S312). If greater than the pre-set threshold (location marked by V in FIG. 4A), the processor 130 determines that the ECG signal is conformed to the VPC (step S313), and the R-wave type is a VPC type. On the contrary, the processor 130 is determined as not conformed and determined as a normal heartbeat (step S314), and the R-wave type is a normal type.

Figure 4B:
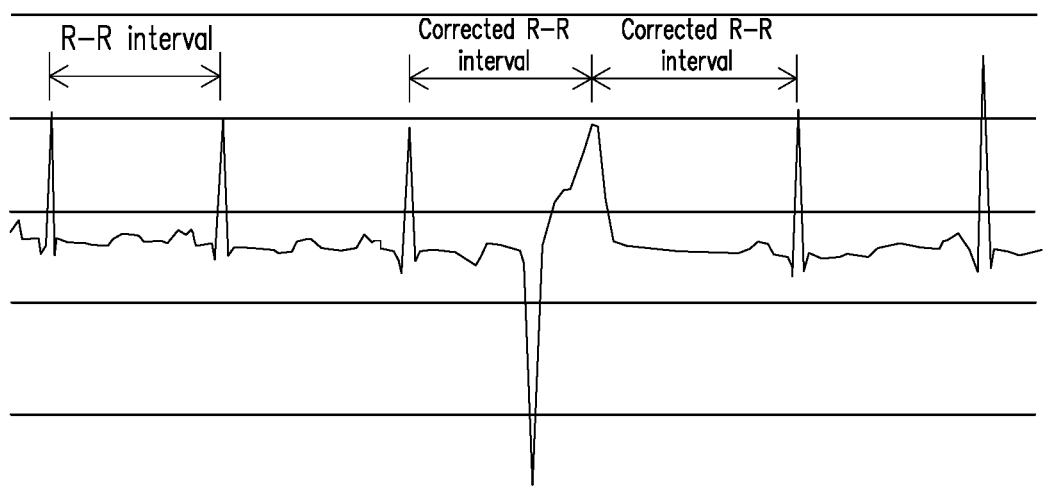

Regarding the assessment of the AF (step S320), an exemplary embodiment of the invention uses the detection method as proposed by the foregoing Document 2. If step S310 determines that premature contraction is conformed (which is, the R-wave type is the VPC type), the processor 130 will correct (or modify) an R position (step S321) of the original ECG signal to obtain the R-R interval that removes the effect of the VPC. For example, FIG. 4B is an example of the ECG signal after correction, the processor 130 corrects the R-wave position of the original ECG signal appearing the VPC feature, and uses the center point between the two adjacent R-wave positions as the R-wave position after correction, thereby obtaining the corrected R-R interval. Next, the processor 130 uses the corrected R-R interval as an input parameter (step S322) of an AF detection algorithm to obtain a sample entropy (step S323), and then decides whether the sample entropy is greater than the pre-set threshold (step S325). If greater than the pre-set threshold, the processor 130 determines that the ECG signal is conformed to the AF (step S326), on the contrary, the processor determines as a normal heart rhythm (step S324). The determined result of the assessment of the VPC modifies the original ECG signal, therefore, a better assessment of the AF is obtained.

Regarding an assessment of the APC (step S330), the processor 130 detects a P-wave position (step S331) based on a morphology. Next, the processor 130 produces seven eigenvalues based on the foregoing QRST waveform which includes a P-R interval, a QRS wavelength, an R-R interval, a next R-R interval, an average R-R interval surrounding twenty R-waves, a standard deviation of the surrounding twenty R-waves, an R-wave height of signal value according to Q and R positions obtained by step S310, and inputs the foregoing eigenvalues to an artificial neural network classification (step S332) (based on Lin, C. H.; Chien, J. C.; Haraikawa, K.; Huang, Y. S.; Guo, H. W.; Shieh, J. S. A modular integrating algorithm for multiple arrhythmia detection. In Proceedings of the IEEE International Conference on Communication Problem-Solving (ICCP), Taipei, Taiwan, 7-9 Sep. 2016; pp. 1-2 (Document 3)), to determine whether is a normal heartbeat (step S333). If yes, the processor determines is a normal heartbeat (step 334). On the other hand, since some features of the APC are similar to that of the AF, it is easy to misjudge as the APC. Therefore, the processor 130 determines whether the determined result of the AF is overlapped (which is, whether steps S310 and S333 are both determined as abnormal heart rhythm) (step S335) based on the existing result of the database. If overlapped, the processor 130 determines that the ECG signal is conformed to the AF, but is not conformed to the APC (step S336), on the contrary, the processor 130 determines that the ECG signal is conformed to the APC (step S337). It should be noted that some features of the APC are also similar to that of the VPC. Therefore, the processor 130 may, in the case where the two determined results are overlapped, also determine that only the VPC is conformed and determine that the assessment of the APC is not conformed.

Regarding the assessment of the VF (step S340), an exemplary embodiment of the invention refers to Lo, M. T.; Lin, L. Y.; Hsieh, W. H.; Ko, P. C. I.; Liu, Y. B.; Lin, C.; Chang, Y. C.; Wang, C. Y.; Young, V. H. W.; Chiang, W. C.; et al. A new method to estimate the amplitude spectrum analysis of ventricular fibrillation during cardiopulmonary resuscitation. Resuscitation 2013, 84, 1505-1511 (Document 4), whereby the processor 130 performs a fast fourier transform on the 2-second ECG signal (step S303) to obtain a periodogram (step S341). The processor 130 defines a target frequency domain (p_vf), a non-target frequency domain (p_nVF) and a second non-target frequency domain (p_nVF2) (step S342) to calculate a ratio (rat2VF) (step S343) of the target frequency domain to the non-target frequency domain. The processor 130 will determine whether the ratio is greater than the corresponding preset threshold (step S344), if not, the processor 130 determines the ECG signal is a normal heart rhythm (step S345), otherwise, the processor 130 determines as an abnormal heart rhythm. Also, based on the existing test result of the database, the processor 130 determines whether the determined result of the AF is overlapped (which is, steps S320 and S344 are both determined as abnormal heart rhythms) (step S346). Whether overlapping or not, the processor 130 will also determine that the ECG signal is conformed to the VF (steps S347 and S348). However, it should be noted that, if overlapping, the processor 130 will further correct the determined result of step S320 as not conformed to the AF.

It should be noted that the algorithm used in steps S310, S320, S330 and S340 are merely examples, and the application of the embodiments of the invention may self-adjusted according to needs. For example, step S340 may use the algorithm proposed by documents such as: Alonso-Atienza, F.; Rojo-Alvarez, J. L.; Rosado-Munoz, A.; Vinagre, J. J.; Garcia-Alberola, A.; Camps-Valls, G. Feature selection using support vector machines and bootstrap methods for ventricular fibrillation detection. Expert Syst. Appl. 2012, 39, 1956-1967 (Document 5), and Anas, E. M. A.; Lee, S. Y.; Hasan, M. K. Exploiting correlation of ECG with certain EMD functions for discrimination of ventricular fibrillation. Comput. Biol. Med. 2011, 41, 110-114 (Document 6). In addition, the sequence of each foregoing assessments may also be changed as needed.

In addition, the invention also provides a non-transitory computer-readable recording medium, whereby the computer-readable recording medium may store a plurality of program code instructions (for example, the ECG signal obtains the program code instructions, the first abnormal rhythm symptom assesses the program code instructions, and the second abnormal rhythm symptom assesses the program code instructions and so on), and after these program code instructions are loaded into the processor 130 of the computation apparatus 100 and executed, the foregoing step of cardiac arrhythmia assessment method may be completed.

In summary, the exemplary embodiments of the invention integrate multiple abnormal rhythm symptom assessments and uses the determined result of a previous assessment to speed up and optimize subsequent assessments. The algorithm and sequence in the exemplary embodiments of the invention may have flexible changes based on needs, and even extend the assessment methods depending on the situation. For a handheld apparatus with less computation performance, the exemplary embodiment of the invention may be applied to achieve an assessment of high accuracy.

Although the invention has been described with reference to the above embodiments, it will be apparent to one of ordinary skill in the art that modifications to the described embodiments may be made without departing from the spirit of the invention. Accordingly, the scope of the invention will be defined by the attached claims and not by the above detailed descriptions.

What is claimed is:

1. A cardiac arrhythmia assessment method, comprising:
obtaining an electrocardiography (ECG) signal;
determining whether the ECG signal is conformed to a first abnormal rhythm symptom; and
determining whether the ECG signal is conformed to a second abnormal rhythm symptom based on the determined result of the first abnormal rhythm symptom, wherein the first abnormal rhythm symptom is different from the second abnormal rhythm symptom,
wherein the step of determining whether the ECG signal is conformed to the second abnormal rhythm symptom based on the determined result of the first abnormal rhythm symptom, comprises:
if the determined result of the first abnormal rhythm symptom is conformed, the feature of the ECG signal is modified and used for deten lining the second abnormal rhythm symptom.

2. The cardiac arrhythmia assessment method according to claim 1, wherein the first abnormal rhythm symptom is a ventricular premature contraction (VPC), and the step of modifying the feature of the ECG signal comprises:
modifying an R-wave position in the ECG signal used for determining the second abnormal rhythm symptom, and accordingly adjust an R-R interval.

3. The cardiac arrhythmia assessment method according to claim 1, wherein the step of determining whether the ECG signal is conformed to the second abnormal rhythm symptom based on the determined result of the first abnormal rhythm symptom, comprises:
   if the determined results of the first abnormal rhythm symptom and the second abnormal rhythm symptom are both abnormal heart rhythm, it is determined that only one of the first abnormal rhythm symptom and the second abnormal rhythm symptom is conformed, and modifying the determined result of another is not conformed.

4. The cardiac arrhythmia assessment method according to claim 3, wherein the first abnormal rhythm symptom is an atrial fibrillation (AF), and the second abnormal rhythm symptom is an atrial premature contraction (APC), and the step of determining that only one of the first abnormal rhythm symptom and the second abnormal rhythm symptom is conformed and modifying the determined result of the other is not conformed, comprises:
   determining only conforming to the AF and not conforming to the APC.

5. The cardiac arrhythmia assessment method according to claim 3, wherein the first abnormal rhythm symptom is a VPC, and the second abnormal rhythm symptom is an APC, and the step of determining that only one of the first abnormal rhythm symptom and the second abnormal rhythm symptom is conformed and modifying the determined result of the other is not conformed, comprises:
   determining only conforming to the VPC and not conforming to the APC.

6. The cardiac arrhythmia assessment method according to claim 3, wherein the first abnormal rhythm symptom is an AF, and the second abnormal rhythm symptom is a ventricular fibrillation (VF), and the step of determining that only one of the first abnormal rhythm symptom and the second abnormal rhythm symptom is conformed and modifying the determined result of the other is not conformed, comprises:
   determining only conforming to the VF and not conforming to the AF.

7. The cardiac arrhythmia assessment method according to claim 1, wherein after determining whether the ECG signal is conformed to the second abnormal rhythm symptom based on the determined result of the first abnormal rhythm symptom, further comprises:
   determining whether the ECG signal is conformed to a third abnormal rhythm symptom based on the determined result of at least one of the first abnormal rhythm symptom and the second abnormal rhythm symptom, wherein the third abnormal rhythm symptom is different from the second abnormal rhythm symptom.

8. A computation apparatus, comprising:
   a transmission interface, obtaining an ECG signal; and
   a processor, coupled to the transmission interface, determining whether the ECG signal is conformed to the first abnormal rhythm symptom, and determining whether the ECG signal is conformed to a second abnormal rhythm symptom based on the determined result of the first abnormal rhythm symptom, wherein the first abnormal rhythm symptom is different from the second abnormal rhythm symptom,
   wherein if the determined result of the first abnormal rhythm symptom is conformed, the processor modifies the feature of the ECG signal, and is used in the determining of the second abnormal rhythm symptom.

9. The computation apparatus according to claim 8, wherein the first abnormal rhythm symptom is a VPC, and the processor modifies an R-wave position in the ECG signal used for determining the second abnormal rhythm symptom, and accordingly adjusts an R-R interval.

10. The computation apparatus according to claim 8, wherein if the determined results of the first abnormal rhythm symptom and the second abnormal rhythm symptom are both abnormal heart rhythms, the processor determines that only one of the first abnormal rhythm symptom and the second abnormal rhythm symptom is conformed, and modifying the determined result of the other is not conformed.

11. The computation apparatus according to claim 10, wherein the first abnormal rhythm symptom is an AF, and the second abnormal rhythm symptom is an APC, and the processor determines that only the AF is conformed and the APC is not conformed.

12. The computation apparatus according to claim 10, wherein the first abnormal rhythm symptom is a VPC, and the second abnormal rhythm symptom is an APC, and the processor determines that only the VPC is conformed and the APC is not conformed.

13. The computation apparatus according to claim 10, wherein the first abnormal rhythm symptom is an AF, and the abnormal rhythm symptom is a VF, and the processor determines that only the VF is conformed and the AF is not conformed.

14. The computation apparatus according to claim 8, wherein the processor determines that the ECG signal is conformed to a third abnormal rhythm symptom based on the determined result in at least one of the first abnormal rhythm symptom and the second abnormal rhythm symptom, wherein the third abnormal rhythm symptom is different from the second abnormal rhythm symptom.

15. A non-transitory computer-readable recording medium, recording a program code which is loaded by a processor of a computation apparatus to perform the following steps:
   obtaining an ECG signal;
   determining whether the ECG signal is conformed to a first abnormal rhythm symptom; and
   determining whether the ECG signal is conformed to a second abnormal rhythm symptom based on the determined result of the first abnormal rhythm symptom, wherein the first abnormal rhythm symptom is different from the second abnormal rhythm symptom,
   wherein the step of determining whether the ECG signal is conformed to the second abnormal rhythm symptom based on the determined result of the first abnormal rhythm symptom, comprises:
   if the determined result of the first abnormal rhytlun symptom is conformed, the feature of the ECG signal is modified and used for determining the second abnormal rhythm symptom.

* * * * *